(12) United States Patent
Charvet

(10) Patent No.: US 9,526,529 B2
(45) Date of Patent: Dec. 27, 2016

(54) BONE SCREW SYSTEMS WITH PRESSURE CAPS HAVING BIASING MEMBERS

(71) Applicant: BLACKSTONE MEDICAL, INC., Lewisville, TX (US)

(72) Inventor: Jose Luis Charvet, South Amboy, NJ (US)

(73) Assignee: BLACKSTONE MEDICAL, INC., Lewisville, TX (US)

( * ) Notice: Subject to any disclaimer, the term of this patent is extended or adjusted under 35 U.S.C. 154(b) by 170 days.

(21) Appl. No.: 14/037,011

(22) Filed: Sep. 25, 2013

(65) Prior Publication Data

US 2015/0088202 A1      Mar. 26, 2015

(51) Int. Cl.
*A61B 17/70* (2006.01)

(52) U.S. Cl.
CPC .................. *A61B 17/7037* (2013.01)

(58) Field of Classification Search
CPC ............ A61B 17/7034; A61B 17/7035; A61B 17/7037; A61B 17/70; A61B 17/7001; A61B 17/7032; A61B 17/7038; A61B 17/7041; A61B 17/7046
See application file for complete search history.

(56) References Cited

U.S. PATENT DOCUMENTS

| | | | |
|---|---|---|---|
| 920,188 A | 5/1909 | Schumacher | |
| 2,987,080 A | 6/1961 | Chandler et al. | |
| 3,477,486 A | 11/1969 | Modrey | |
| 5,505,732 A | 4/1996 | Michelson | |
| 5,797,911 A * | 8/1998 | Sherman et al. | 606/270 |
| 6,485,491 B1 * | 11/2002 | Farris | A61B 17/7002 606/250 |
| 7,250,052 B2 * | 7/2007 | Landry | A61B 17/1604 606/86 A |
| 7,338,491 B2 * | 3/2008 | Baker | A61B 17/7032 606/266 |
| 7,377,923 B2 * | 5/2008 | Purcell | A61B 17/7038 606/248 |

(Continued)

FOREIGN PATENT DOCUMENTS

| | | |
|---|---|---|
| FR | 2954689 A1 | 7/2011 |
| WO | 2011/133160 A1 | 10/2011 |

OTHER PUBLICATIONS

International Search Report and Written Opinion, PCT/US2012/049180, dated Oct. 26, 2012, 9 pages.

(Continued)

*Primary Examiner* — Lynnsy Summitt
(74) *Attorney, Agent, or Firm* — Baker & McKenzie LLP

(57) ABSTRACT

A spinal fixation system comprising a bone screw, a body, and a pressure cap. The bone screw may comprise a head at a proximal end and a bone connection element at a distal end. The body may comprise a proximal end, a distal end, a mounting rod receiving channel at the proximal end and a bone screw head receiving channel at the distal end. A proximal end of the pressure cap may comprise two side walls disposed apart from each other and one biasing member on each side wall. A distal end of the pressure cap may comprise a surface operable to contact at least a portion of the head of the bone screw. The pressure cap may be operable to exert pressure on the bone screw when a mounting rod is biased against the proximal end of the pressure cap.

24 Claims, 11 Drawing Sheets

(56) References Cited

U.S. PATENT DOCUMENTS

| | | | |
|---|---|---|---|
| 7,749,258 B2 | 7/2010 | Biedermann et al. | |
| 7,766,946 B2 * | 8/2010 | Bailly | A61B 17/7032 606/267 |
| 7,811,310 B2 * | 10/2010 | Baker | A61B 17/7032 606/267 |
| 7,922,725 B2 | 4/2011 | Darst Rice et al. | |
| 7,942,909 B2 * | 5/2011 | Hammill, Sr. | A61B 17/7037 606/267 |
| 7,951,173 B2 * | 5/2011 | Hammill, Sr. | A61B 17/7034 606/267 |
| 8,066,745 B2 | 11/2011 | Kirschman | |
| 8,100,946 B2 * | 1/2012 | Strausbaugh | A61B 17/7032 606/266 |
| 8,142,436 B2 | 3/2012 | Kirschman | |
| 8,167,910 B2 * | 5/2012 | Nilsson | A61B 17/7032 606/264 |
| 8,221,472 B2 * | 7/2012 | Peterson | A61B 17/7032 606/266 |
| 8,419,778 B2 | 4/2013 | Barry | |
| 8,430,914 B2 | 4/2013 | Spratt et al. | |
| 8,882,817 B2 * | 11/2014 | Jones | A61B 17/7037 606/264 |
| 8,951,290 B2 * | 2/2015 | Hammer | A61B 17/7034 606/267 |
| 2002/0120275 A1 | 8/2002 | Schmieding et al. | |
| 2003/0105460 A1 | 6/2003 | Crandall et al. | |
| 2003/0231927 A1 | 12/2003 | Hale | |
| 2004/0176766 A1 * | 9/2004 | Shluzas | 606/65 |
| 2004/0186483 A1 | 9/2004 | Bagby | |
| 2004/0225289 A1 * | 11/2004 | Biedermann et al. | 606/61 |
| 2005/0043735 A1 | 2/2005 | Ahmad | |
| 2006/0142762 A1 | 6/2006 | Michelson | |
| 2006/0200131 A1 * | 9/2006 | Chao et al. | 606/61 |
| 2007/0016200 A1 * | 1/2007 | Jackson | A61B 17/7005 623/17.16 |
| 2007/0078460 A1 | 4/2007 | Frigg et al. | |
| 2007/0118123 A1 | 5/2007 | Strausbaugh et al. | |
| 2007/0239159 A1 | 10/2007 | Altarac et al. | |
| 2007/0281274 A1 | 12/2007 | Schraffran et al. | |
| 2008/0009862 A1 * | 1/2008 | Hoffman | 606/61 |
| 2008/0147129 A1 * | 6/2008 | Biedermann et al. | 606/308 |
| 2009/0076552 A1 | 3/2009 | Tornier | |
| 2009/0198280 A1 | 8/2009 | Spratt et al. | |
| 2009/0281550 A1 | 11/2009 | Keller | |
| 2009/0306721 A1 | 12/2009 | Kirschman | |
| 2010/0152785 A1 | 6/2010 | Forton et al. | |
| 2010/0212460 A1 | 8/2010 | Buss et al. | |
| 2010/0298891 A1 | 11/2010 | Jackson | |
| 2010/0305621 A1 | 12/2010 | Wang et al. | |
| 2010/0312288 A1 * | 12/2010 | Hammill et al. | 606/305 |
| 2011/0046683 A1 * | 2/2011 | Biedermann | A61B 17/7035 606/305 |
| 2011/0077694 A1 * | 3/2011 | Biedermann et al. | 606/305 |
| 2011/0152940 A1 | 6/2011 | Frigg et al. | |
| 2011/0160778 A1 * | 6/2011 | Elsbury | A61B 17/7037 606/305 |
| 2011/0172714 A1 | 7/2011 | Boachie-Adjei et al. | |
| 2011/0178559 A1 | 7/2011 | Barry | |
| 2011/0263945 A1 | 10/2011 | Peterson et al. | |
| 2011/0282399 A1 * | 11/2011 | Jackson | A61B 17/702 606/305 |
| 2012/0031792 A1 | 2/2012 | Petit | |
| 2012/0046699 A1 * | 2/2012 | Jones | A61B 17/7037 606/305 |
| 2013/0096624 A1 | 4/2013 | Di Lauro et al. | |
| 2013/0110176 A1 * | 5/2013 | Rezach et al. | 606/305 |
| 2013/0131734 A1 * | 5/2013 | Longtain | A61B 17/7037 606/305 |
| 2013/0226243 A1 | 8/2013 | Kraus | |
| 2015/0272627 A1 * | 10/2015 | Jackson | A61B 17/7032 606/305 |

OTHER PUBLICATIONS

U.S. Office Action, U.S. Appl. No. 14/092,154, dated Dec. 24, 2015, 11 pages.

International Search Report and Written Opinion, PCT/US2014/061293, dated Jan. 23, 2015, 12 pages.

U.S. Office Action, U.S. Appl. No. 13/196,635, dated May 8, 2015, 28 pages.

U.S. Office Action, U.S. Appl. No. 14/059,203, dated May 18, 2015, 46 pages.

* cited by examiner

BONE SCREW SYSTEMS WITH PRESSURE CAPS HAVING BIASING MEMBERS

FIELD OF THE DISCLOSURE

The present disclosure relates, in some embodiments, to spinal fixation systems. More specifically, the present disclosure relates, in some embodiments, to spinal fixation systems operable for use on pedicle portions of a spine.

BACKGROUND OF THE DISCLOSURE

Various systems exist for connecting fastener elements (e.g., pedicle screws) to bones for the purposes vertebral fixation. Such systems may use a plurality of bone screws fitted in bodies, wherein a plurality of bodies are aligned using a mounting rod.

A spinal fixation system may comprise several components with various degrees of stability or various degrees of movement between the components themselves or between the components and the bones to which they are affixed. For example, the connection between the bones and the fastener may have a degree of stability. Greater stability may help promote a more secure system and a more secure fixation for multiple segments of the spine.

In some surgical proceedings, several parts may be used to be assemble the spinal fixation system. A high number of components may be inconvenient for the surgeon and may be dangerous for the patient if any component becomes unsecured or breaks off from the spinal fixation system.

In some surgical proceedings, the components intended to be used for the spinal fixation system may often be preselected. Such selection may be made based on a number of factors such as the particular dimensions of the components and the anatomical location for the fixation of the system. However, during some surgical procedures, the preselected components may be determined to not actually be ideal. For example, a body selected as part of the spinal fixation system may be determined to be too big or too small for a particular situation or particular patient. When this is the case, replacing the body may requiring removing the secured bone screw from the patient's bones. Then, a new body may be selected and fitted with the bone screw. Such procedures may be inconvenient for the surgeon and may be dangerous for the patient.

In some surgical proceedings, the spinal fixation system may be used in pediatric settings or on pediatric patients. Traditional spinal fixation systems may be too large to be fitted ideally or securely in pediatric patients.

SUMMARY

Accordingly, a need has arisen for improved spinal fixation systems that may allow for fewer components, may allow for a body to be interchanged without removal of the bone screw from a bone, and may be suitable for pediatric settings.

The present disclosure relates, according to some embodiments, to a spinal fixation system comprising a bone screw, a body, and a pressure cap. A bone screw may comprise a head at a proximal end and a bone connection element at a distal end. A body may comprise a proximal end, a distal end, a mounting rod receiving channel at the proximal end and a bone screw head receiving channel at a distal end. A proximal end and a distal end may be disposed along a longitudinal axis. A proximal portion of a mounting rod receiving chamber may comprise an internal thread operable to receive a compression element therein. A proximal end of a pressure cap may comprise two side walls disposed apart from each other and at least one biasing member on each side wall. A distal end of a pressure cap may comprise a surface operable to contact at least a portion of a head of a bone screw. A pressure cap may be configured to be disposed within a body and between a mounting rod and a bone screw. A pressure cap may be operable to exert pressure on a bone screw when a mounting rod is biased against a proximal end of a pressure cap.

In some embodiments, a head of a bone screw may have a substantially spherical surface. In some embodiments, a bone connection element may comprise an external thread operable to be secured into a pedicle portion of a spine. In some embodiments, a mounting rod receiving channel may be operable to receive a mounting rod at an angle substantially orthogonal to a longitudinal axis of the body. In some embodiments, a bone screw head receiving channel may be sized to securely receive a bone screw head. In some embodiments, a proximal end of a pressure cap may comprise a partially curved surface that may be disposed between sidewalls and may be operable to be aligned with a portion of a mounting rod. In some embodiments, a bone screw, a body, a compression element, a mounting rod, a pin, and a pressure cap may each comprise material independently selected from the group consisting titanium, titanium alloy, stainless steel, cobalt chrome, or any combination thereof. In some embodiments, a body may further comprise a pin hole disposed orthogonal to a longitudinal axis of a body. In some embodiments, a pressure cap may further comprise a pin hole disposed orthogonal to a longitudinal axis of the body. In some embodiments, a pin hole of the body and a pin hole of a pressure cap may align and may be operable to receive a pin therein. In some embodiments, a body may further comprise an undercut adjacent to a mounting rod receiving channel and distal to an internal thread. In some embodiments, each of sidewalls may comprise a radial protrusion operable to fit within an undercut when a pressure cap is disposed within a body. In some embodiments, a biasing member may be operable to bias a pressure cap against a head of the bone screw. In some embodiments, a biasing member may be a leaf spring. In some embodiments, a leaf spring may be substantially monolithic with a proximal portion of a pressure cap. In some embodiments, a head of a bone screw may further comprise a threaded region that may be operable to engage or disengage with a threaded recess of a distal end of a body. In some embodiments, a threaded region may be operable to engage or disengage with a threaded recess by means of a full turn. In some embodiments, a body may have a monolithic construction. In some embodiments, a body may be about 0.45 inches high. In some embodiments, a pressure cap may be about 0.2 inches high. In some embodiments, a body may have a two-piece construction. In some embodiments, a body may be about 0.36 inches high. In some embodiments, a pressure cap may be about 0.25 inches high. In some embodiments, a body may further comprise an undercut adjacent to a mounting rod receiving channel and distal to an internal thread. In some embodiments, sidewalls may be disposed adjacent to a chordal recess on a proximal end of a pressure cap. In some embodiments, a proximal end of a pressure cap may be operable to fit within an undercut when a pressure cap may be disposed within a body.

The present disclosure relates, in some embodiments, to methods of affixing a bone screw system to a bone, such as a pedicle portion of a spine. A method may comprise providing a bone screw, wherein a bone screw may comprise a head at a proximal end, a bone connection element at a distal end, and a threaded region at the head. A method may further comprise providing a body wherein a body comprises a proximal end, a distal end, a mounting rod receiving channel disposed at a proximal end of a body; a bone screw head receiving channel disposed at a distal end of a body, an undercut, and a threaded recess on the distal end of a body. A proximal end and a distal end may be disposed along a longitudinal axis. A method may further comprise securing a threaded region with a threaded recess by means of a full turn. A method may further comprise securing a bone connection element of a bone screw to a bone. The method may further comprise providing a pressure cap. The pressure cap may comprise a proximal end and a distal end. A proximal end may comprise at least two radial protrusions disposed apart from each other, and at least one biasing member disposed on each radial protrusion. A method may further comprise disposing a pressure cap in the body through a mounting rod receiving channel. A method may further comprise securing a pressure cap in a body by means of a ¼ turn such that radial protrusions are received into an undercut. In some embodiments, a method may further comprise disengaging a threaded region from a threaded recess. The disengagement may be accomplished by means of a full turn of the body.

BRIEF DESCRIPTION OF THE DRAWINGS

Some embodiments of the disclosure may be understood by referring, in part, to the present disclosure and the accompanying drawings, wherein.

DETAILED DESCRIPTION

The present disclosure relates, in some embodiments, to bone screw systems. More specifically, the present disclosure relates, in some embodiments, to pedicle screw systems that may comprise a pressure cap, wherein the pressure cap may comprise at least one biasing member.

In some embodiments, the present disclosure may relate to a modular pedicle screw that may be easily disassembled. More specifically, in some embodiments, the present disclosure may relate to a pedicle screw system wherein a body of a system may be easily removed from a bone screw even after a bone screw may have been affixed or secured to a bone.

In some embodiments, the present disclosure may relate to a pedicle screw system operable for use in pediatric settings. More specifically, in some embodiments, the present disclosure may relate to a pedicle screw system wherein the size and design of the components of the system may be advantageous in pediatrics settings or when used on pediatric patients.

Figure 1:
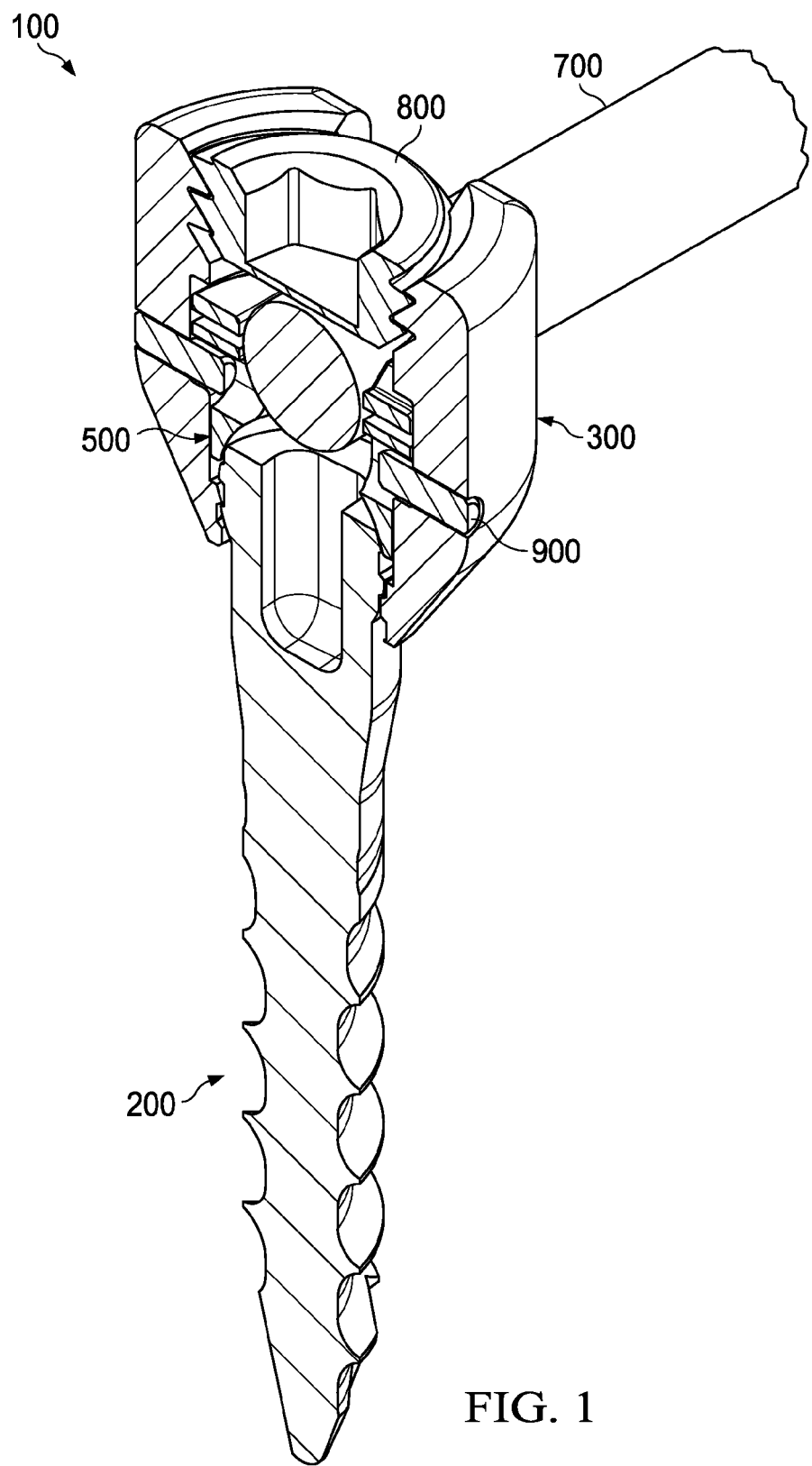
FIG. 1 illustrates a cross-sectional view of a pedicle screw system according to a specific example embodiment of the disclosure.

Referring now to FIG. 1, a cross-sectional view of a pedicle screw system according to a specific example embodiment of the disclosure is illustrated. As seen in FIG. 1, pedicle screw system 100 according to the present disclosure may comprise bone screw 200, body 300, pressure cap 500, mounting rod 700, compression element 800, and pin 900. Additional features and advantages of various embodiments of the present disclosure will become apparent to one of ordinary skill in the art having the benefit of the present disclosure and the description herein.

Figure 2:
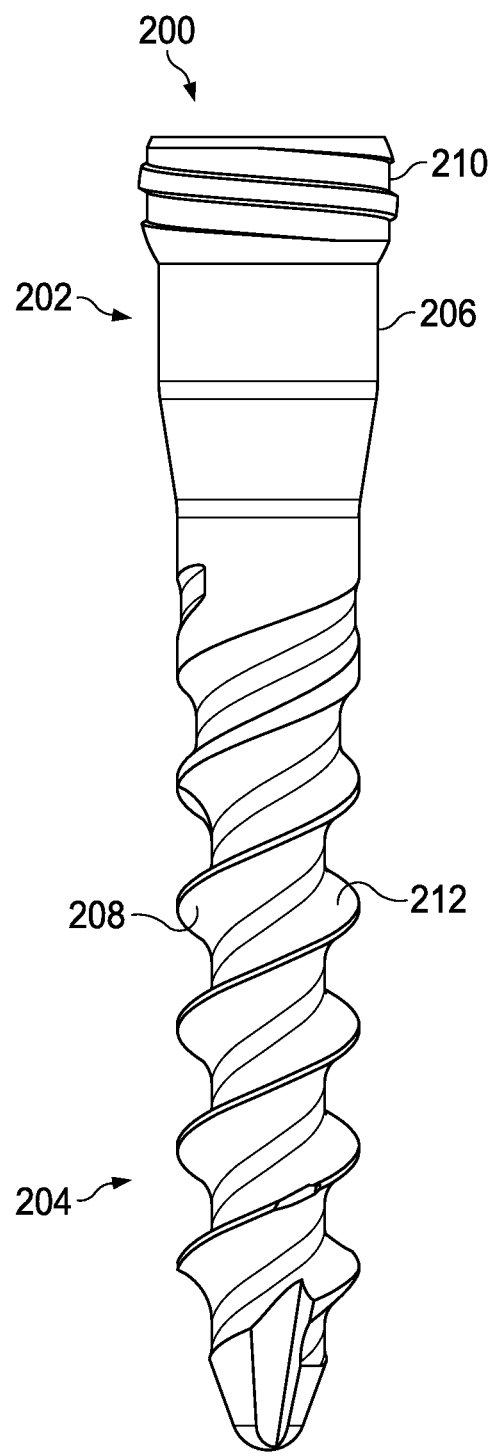
FIG. 2 illustrates a profile view of a pedicle screw according to a specific example embodiment of the disclosure.

Referring now to FIG. 2, a profile view of a pedicle screw according to a specific example embodiment of the disclosure is shown. As seen in FIG. 2, in some embodiments, bone screw 200 may comprise proximal end 202 and distal end 204. Head 206 may be disposed at proximal end 202. Bone connection element 208 may be disposed at distal end 204. In some embodiments, head 206 may be substantially spherical in shape (not pictured.) One of ordinary skill in the art would appreciate that, in such embodiments, the spherical shape of head 206 may allow bone screw 200 to be easily received into body 300 and may allow bone screw 200 to be more securely fitted or seated into a distal end of body 300. Head 206 of bone screw 200 having a substantially spherical geometry may more securely fit into a distal end of body 300, 400 provided that bone screw head receiving channel 308, 408 may have a corresponding spherical geometry. Such features may advantageously provide for greater ease during surgical procedures or during assembly of spinal fixation system 100.

According to some embodiments, head 206 of bone screw 200 may further comprise threaded region 210. Threaded region 210 may be operable to engage or disengage with threaded recess 314 on distal end of body 300 (see FIG. 3A). Different engagement mechanisms may be used to engage or disengage threaded region 210 with threaded recess 314. In some embodiments, threaded region 210 and threaded recess 314 may be designed to fully engage or "lock" upon at least a partial turn of threaded region 210 into threaded recess 314. In some embodiments, threaded region 210 and threaded recess 314 may engage upon a full turn. In some embodiments, body 300 and bone screw 200 may be easily engaged or disengaged. Accordingly, such features may advantageously allow for body 300 to be disengaged from bone screw 200 after bone screw 200 has already been secured into a bone. For example, during a surgical procedure a surgeon may fit bone screw 200 with a selected body. Then, the surgeon may secure this combination of bone screw 200 and a selected body into a bone region by, for example, screwing bone connection element 208 into a bone. However, after securing bone connection element 208 into a bone, it may become apparent that a body selected was not ideal or that a differently designed or differently sized body may be more appropriate. A different body may be more appropriate as it may promote a more secure fit of spinal fixation system 100 with a bone, or it may promote a better alignment of a mounting rod 700 through a plurality of bodies 300.

According to some embodiments, bone connection element 208 may comprise external thread 212. External thread 212 may extend from a base of head 206 of bone screw 200 to an end of distal end 204. External thread 212 may be operable to allow bone connect element 208 to be secured into a bone, such as a pedicle portion of a spine. Dimensions of bone connection element 208 and external thread 212 may be varied to achieve different advantages. Explained further, the dimensions, such as the pitch, lead angle, or helix angle of bone connection element 208 and external thread 212 may be varied to promote greater stability of spinal fixation system 100 or promote greater ease in securing bone screw 200 into a bone.

According to some embodiments, threaded region 210 and threaded recess 314 may comprise different dimensions or thread designs than external thread 212 of bone connection element 208. In some embodiments, the threading design of threaded region 210 may run in a direction opposite to the threading design of external thread 212. For example, threaded region 210 may run in a clockwise direction while external thread 212 may run in a counterclockwise direction. Differing the thread designs of threaded region 210 and external thread 212 may allow for threaded recess 314 to disengage from threaded region 210 without interfering with the engagement between external thread 212 and a bone. As previously explained, such a design may allow a selected body to be disengaged after bone connection element 208 has been secured in a bone and for a different body to be reattached or engaged to bone screw 200 without the need to remove bone connection element 208 from the bone.

According to some embodiments, the length of bone screw 200 may be varied to fit particular design needs. For example, bone screw 200 used for the cervical and upper thoracic regions may have a smaller size or radius than bone screw 200 used for the lumbar or lower thoracic regions. As another example, bone screw 200 used in pediatric settings may have a smaller size or radius than bone screw 200 used in spinal fixation systems 100 intended for adult patients. In some embodiments, the length of bone screw 200 may be about 0.75 inches to about 1.5 inches. In some embodiments, the length of bone screw 200 may be about 1.09 inches.

Figure 3A:
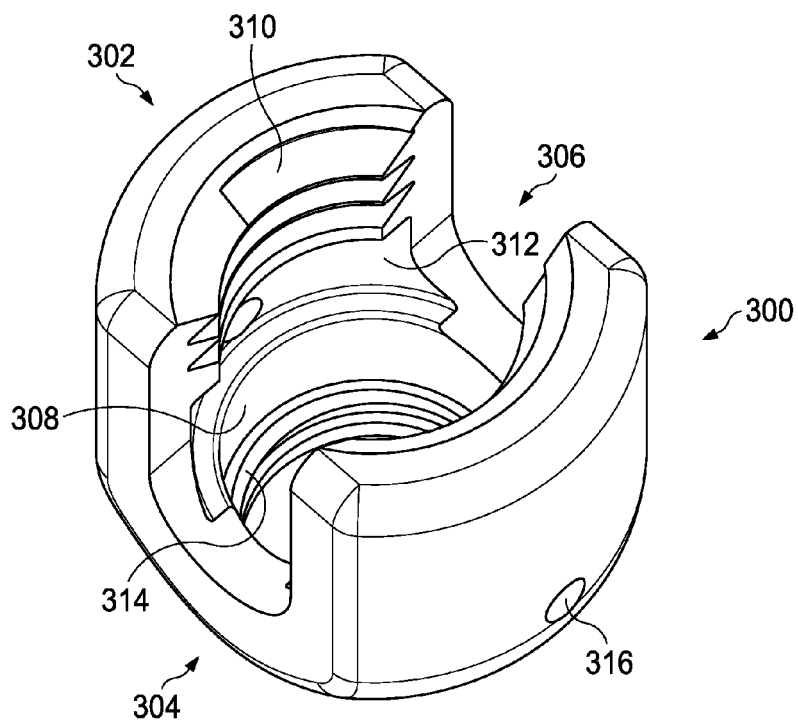
FIG. 3A illustrates an perspective view of a body according to a specific example embodiment of the disclosure.
Figure 3B:
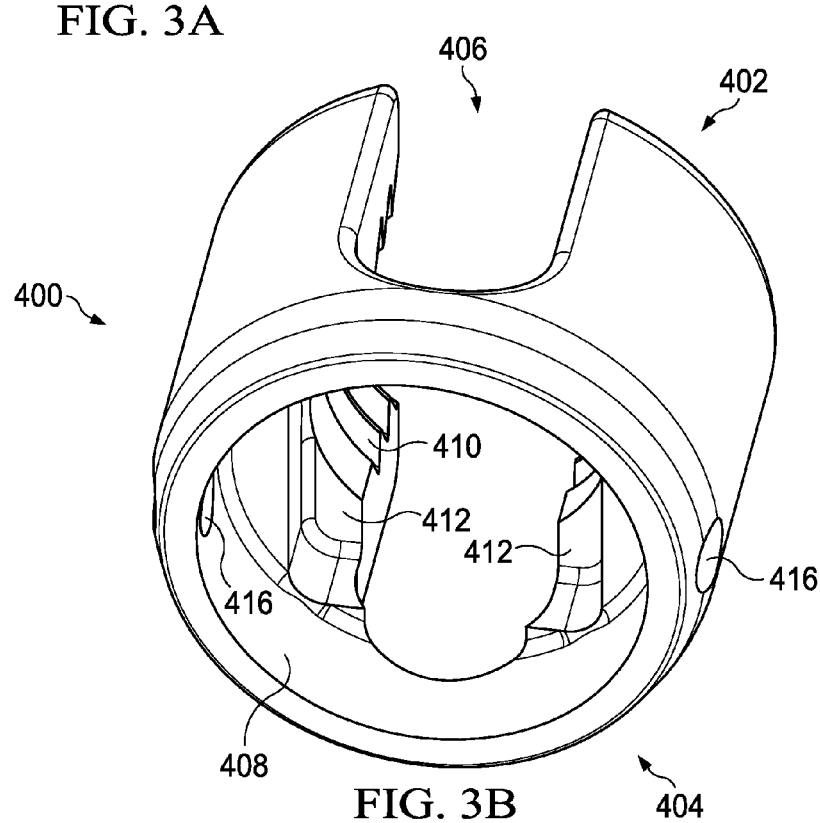
FIG. 3B illustrates a different perspective view of a body according to another specific example embodiment of the disclosure.

Referring now to FIG. 3A and FIG. 3B, perspective views of bodies according to specific example embodiments of the present disclosure are shown. More specifically, FIG. 3A illustrates a perspective view from proximal end 302 of body 300 that may allow for convenient disassembling of bone screw 200 from body 300. FIG. 3B illustrates a perspective view from distal end 404 of body 400 that may be suitable for pediatric use. In both embodiments, body 300, 400 may comprise proximal end 302, 402 and distal end 402, 404. Proximal end 302, 402 and distal end 304, 404 may be disposed along a longitudinal axis.

Bodies 300, 400 may be substantially cylindrical articles with hollowed-out interiors. The hollowed-out interiors may serve to receive bone screws 200 therein. Bodies 300, 400 may also receive mounting rod 700, compression element 800, and pin 900.

Bodies 300, 400 may further comprise mounting rod receiving channel 306, 406 disposed at proximal end 302, 402 of the body 300, 400. Mounting rod 700 may be received into mounting rod receiving channel 306, 406 of body 300, 400 at an angle substantially orthogonal to the longitudinal axis of body 300, 400. The size and design of the mounting rod receiving channel 306, 406 may be varied for various functional and design reasons. For example, a larger mounting rod 700 may be deemed more appropriate for a particular spinal fixation system such as a lumbar region of a spine where weight loading may be greater. Accordingly, body 300, 400 with a larger or wider mounting rod receiving channel 306, 406 may be chosen to accommodate the larger mounting rod 700. Such variations may be made without departing from the description herein.

Bodies 300, 400 may further comprise bone screw head receiving channel 308, 408 disposed at distal end 304, 404 of body 300, 400. The size of bone screw receiving channel 308, 408 may be varied for various functional and design reasons. For example, bone screw 200 with larger head 206 may be deemed more appropriate for particular spinal fixation systems. Accordingly, body 300, 400 with larger or wider bone screw head receiving channel 308, 408 may be chosen to accommodate the larger bone screw head 206. Such variations may be made without departing from the description herein.

Figure 7A:
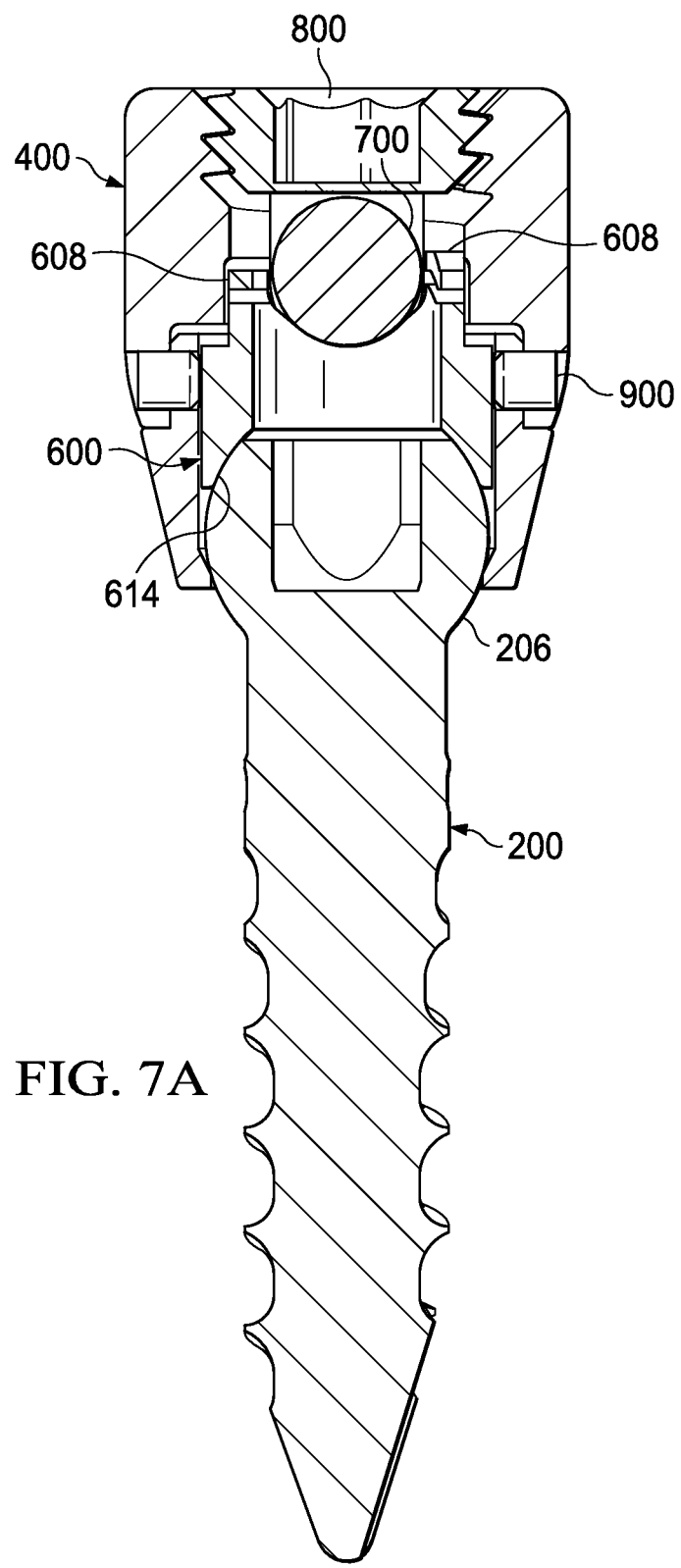
FIG. 7A illustrates a profile cross-sectional view of a pedicle screw system according to a specific example embodiment of the disclosure.

Proximal portion 302, 402 of mounting rod receiving channel 306, 406 may comprise internal thread 310, 410 for receiving compression element 800 (see FIG. 7A). Dimensions and designs of internal thread 310, 410 may be varied for various functional and design reasons. For example, a different internal thread 310, 410 may be used to correspond with external thread of a particular compression element 800. Such variations may be made without departing from the description herein.

Bodies 300, 400 may further comprise pin hole 316, 416 that may be disposed orthogonal to the longitudinal axis of bodies 300, 400. Described further, each body 300, 400 may comprise two pin holes 316, 416 disposed on either side of the body. Two pin holes 316, 416 may then align with two pin holes 516, 616 on either side of seated pressure cap 500, 600. The alignment of pin holes 516 in pressure cap 500, 600 and body 300, 400 may allow pin 900 to be received therein. Received pin 900 may allow spinal fixation system 100 to have a more secured and stable assembly. The use of pin 900 may or may not be necessary or advantageous depending on the particular requirements of spinal fixation system 100. For example, the inclusion of pin 900 may allow for added security. However, the inclusion of pin 900 may also result in an increase in the number of independent components in spinal fixation system 100. Embodiments of the present disclosure may or may not include a pin 900. Such variations may be made without departing from the description herein.

In the exemplary embodiment illustrated by FIG. 3A, body 300 may further comprise threaded recess 314. Threaded recess 314 may be disposed at distal end 304 of body 300. Threaded recess 314 or threaded lip may comprise a substantially circular or spiral recess that circumscribes distal end 304 of body 300 where bone screw 200 and body 300 may mate. In some embodiments, threaded recess 314 may be operable to engage or disengage with threaded region 210 of head 206 of bone screw 200. In some embodiments, threaded recess 314 may be operable to engage or disengage with threaded region 210 of head 206 of bone screw 200 by means of a full turn. As previously described, such features may advantageously allow for body 300 to be disengaged from bone screw 200 after bone screw 200 has already been secured into a bone. For example, during a surgical procedure a surgeon may fit bone screw 200 with a selected body. Then, the surgeon may secure this combination of bone screw 200 and the selected body into a bone region by, for example, screwing bone connection element 208 into the bone. However, after securing bone connection element 208 into the bone, it may become apparent that the body selected was not ideal or that a differently designed or differently sized body may be more appropriate. A different body may be more appropriate as it may promote a more secure fit of spinal fixation system 100 with the bone, or it may promote a better alignment of mounting rod 700 through a plurality of bodies 300.

In the exemplary embodiment illustrated by FIG. 3A, body 300 may further comprise undercut 312. Undercut 312 may be disposed adjacent to mounting rod receiving channel 306 and may be distal to internal thread 310. Described further, undercut 312 may comprise at least one internal recess within body 300. In some embodiments, undercut 312 may be an annular or curved recess. Internal recess may be disposed near the distal portion of mounting rod receiving channel 306. A distal portion of mounting rod receiving channel 306 may be above bone screw head receiving channel 308, and may be the position where proximal end 502 of pressure cap 500 may be disposed when placed in body 300. Accordingly, undercut 312 may comprise at least one recess that may receive a portion of proximal end 502 of pressure cap 500. The fitting of proximal end 502 of pressure cap 500 within undercut 312 may help promote a secure locking of pressure cap 500 within body 300. Accordingly, a more stable and secure spinal fixation system may be provided. The size and shape of undercut 312 may be varied for various functional and design reasons without departing from the description herein.

In the exemplary embodiment illustrated by FIG. 3B, body 400 may further comprise undercut 412. Undercut 412 may be disposed adjacent to mounting rod receiving channel 406 and may be distal to internal thread 410. Described further, undercut 412 may comprise at least one internal recess within body 400. In some embodiments, a plurality of undercuts 412 may form a substantially square pocket geometry within body 400. The at least one undercut 412 may be disposed near a distal portion of mounting rod receiving channel 406. A distal portion of mounting rod receiving channel 406 may be above bone screw head receiving channel 408, and may be the position where proximal end 602 of the pressure cap 600 may be disposed when placed in the body 400. Undercuts 412 of the example embodiment illustrated in FIG. 3B may be operable to receive proximal end 602 of pressure cap 600. Pressure cap 600 configured or designed to fit with the body 400 illustrated in FIG. 3B may have chordal recesses at proximal end 602 of pressure cap 600. The chordal recesses on proximal end 602 may form a substantially square-like geometry at proximal end 602 of pressure cap 600. Accordingly, the substantially square-like geometry at proximal end 602 of pressure cap 600 may be operable to fit into a corresponding square-like pocket formed by undercuts 412 disposed within body 400. The size and shape of undercut 412 may be varied for various functional and design reasons without departing from the description herein.

Bodies 300, 400 in the exemplary embodiments illustrated by FIG. 3A and FIG. 3B may comprise a single-piece construction or a multi-piece construction. Explained further, body 300, 400 may be single article or body 300, 400 may be further comprised of multiple articles that may fit together to form the substantially hollowed out cylinder geometry of body 300, 400. In some embodiments, body 300, 400 having a single-piece construction may have a substantially monolithic construction. Accordingly, body 300, 400 may have a uniform composition or be made of or machined out of one particular material. In exemplary embodiments, bodies 300, 400 comprising a multi-piece construction may comprise two pieces. However, in some embodiments, more pieces may be used. In some embodiments, body 300 operable to be disassembled through a full turn of threaded lip 314 of body 300 may comprise a single-piece construction. In some embodiments, body 400 operable to be used in pediatric settings may comprise a two-piece construction. Illustrative examples of body 400 with a two-piece construction may be seen in FIG. 7A and FIG. 7B.

In some embodiments, the height of body 300, 400 may be about 0.4 inches to 0.6 inches high. In some embodiments utilizing a 4.0 mm rod, body 300, 400 may be about 0.45 inches high. In some embodiments utilizing a 6.0 mm rod, body 300, 400 may be about 0.53 inches high. The size and shape of body 300, 400 may be varied for various functional and design reasons without departing from the description herein. In some embodiments, body 300, as used in spinal fixation system 100 wherein body 300 may be easily disengaged from bone screw 200 secured in a bone, may have a height of about 0.45 inches. In some embodiments, body 400, as used in a pediatric setting or in a pediatric patient, may have a height of about 0.36 inches.

Figure 4A:
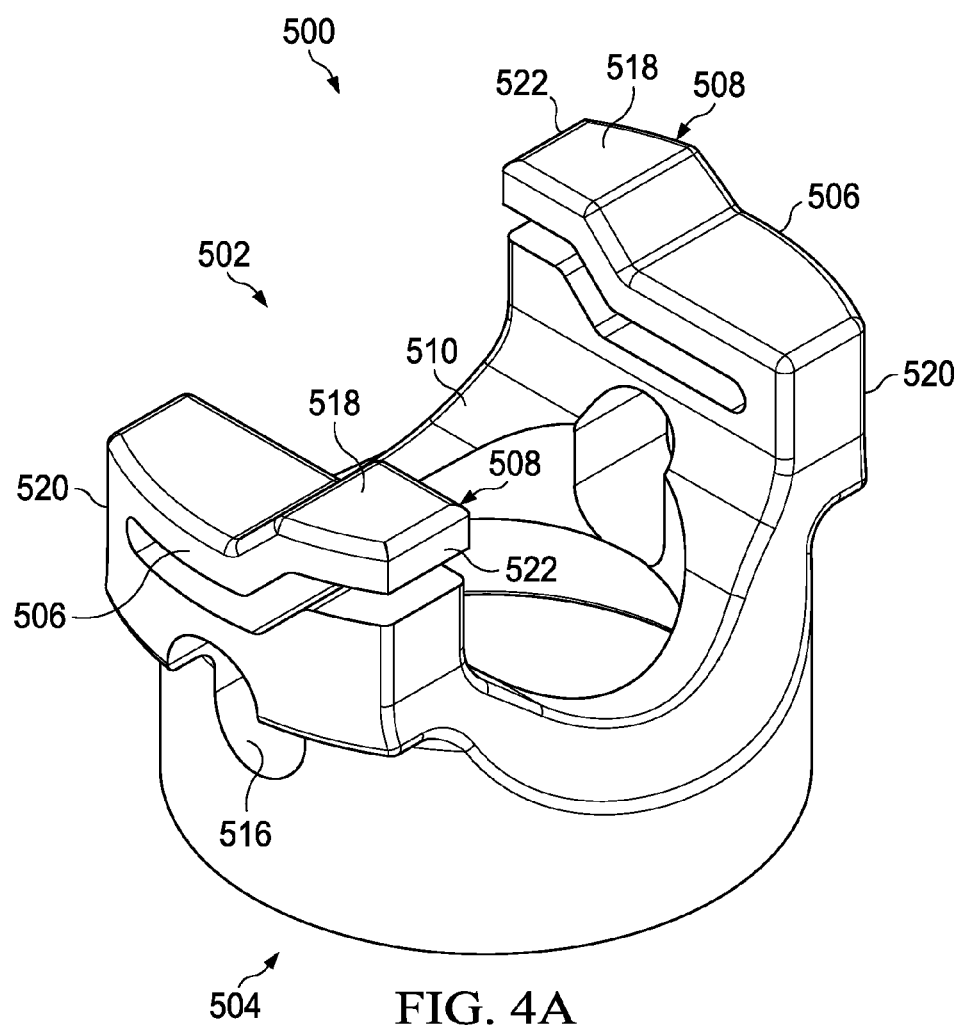
FIG. 4A illustrates a perspective view of a pressure cap according to a specific example embodiment of the disclosure.
Figure 4B:
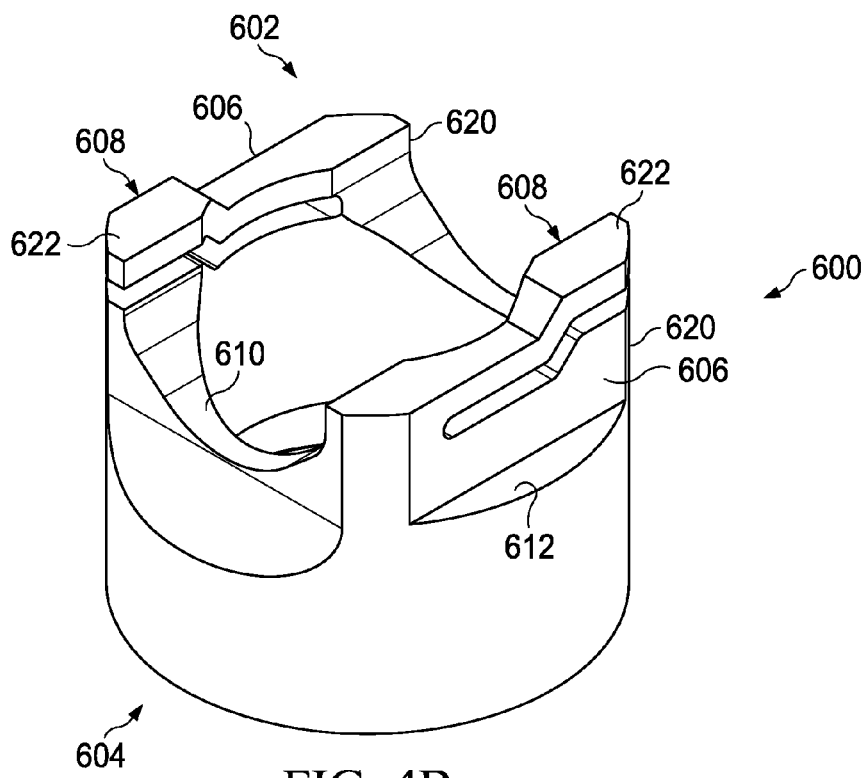
FIG. 4B and FIG. 4C illustrate perspective views of a pressure cap according to another specific example embodiment of the disclosure.
Figure 4C:
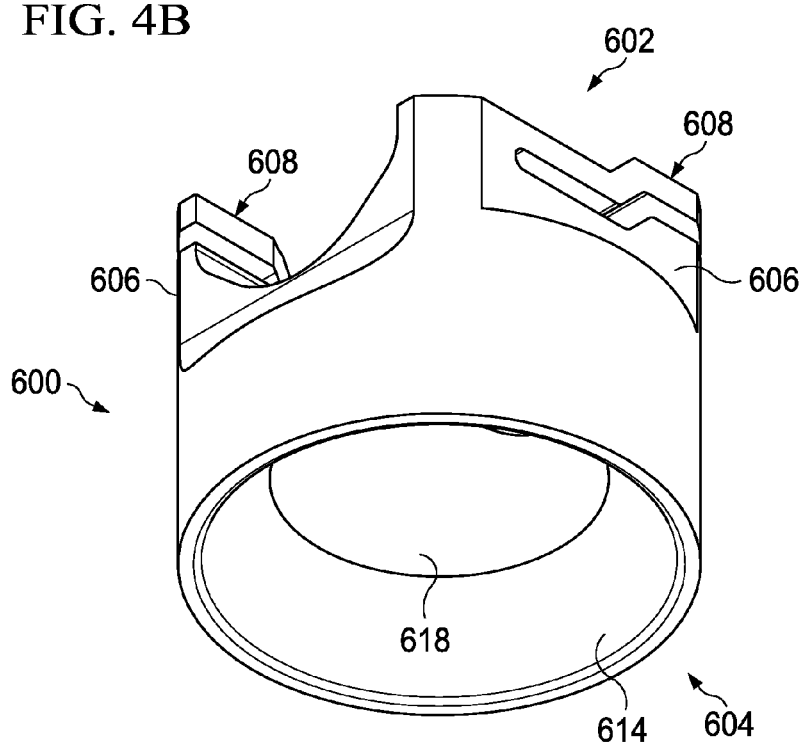

Referring now to FIG. 4A, FIG. 4B, and FIG. 4C, perspective views of pressure caps according to specific example embodiments of the disclosure are illustrated. More specifically, in some embodiments, pressure cap 500 of FIG. 4A may be operable for use in spinal fixation system 100 wherein body 300 may be easily disengaged from bone screw 200 that may already be secured in a bone. In some embodiments, pressure cap 600 of FIG. 4B and FIG. 4C may be operable for use in spinal fixation system 100 which may suitable for pediatric settings.

In some embodiments, pressure cap 500, 600 may comprise proximal end 502, 602 and distal end 504, 604. Pressure cap 500, 600 may be a substantially cylindrically shaped article operable to be fitted on top of bone screw 200 inside the receiving channels of body 300, 400. Pressure cap 500, 600 may be configured to be disposed within body 300, 400 and between mounting rod 700 and bone screw 200. Pressure cap 500, 600 may be operable to exert pressure on bone screw 200 when mounting rod 700 is biased against or pressed down on proximal end 502, 602 of pressure cap 500, 600. Accordingly, pressure cap 500, 600 may promote a more secure and sealed fit of components within bodies 300, 400 of spinal fixation system 100.

In some embodiments, proximal end 502, 602 of pressure cap 500, 600 may comprise partially curved surface 510, 610. Partially curved surface 510, 610 may be a downward groove or downward curve on proximal end 502, 602 of pressure cap 500, 600. Curved surface 510, 610 may advantageously allow mounting rod 700 to sit or align against it. Mount rod 900 may have a substantially cylindrical geometry. Accordingly, the portion of mounting rod 700 that may mate with or may be pressed on proximal end 502, 602 of pressure cap 500, 600 may have a curvature corresponding to the radius or cylindrical geometry of mounting rod 700. Thus, curved surface 510, 610 advantageously allows mounting rod to rest or be aligned more securely or in a more fitted manner on the top of pressure cap 500, 600. The curvature of the curved surface 510, 610 may be varied for various functional and design reasons without departing from the description herein. For example, the curvature may be varied so as to contour or align more properly with mounting rod 900 having a different radius.

In some embodiments, pressure cap 500 may further comprise at least one pin hole 516. For example, FIG. 4A illustrates pin hole 516. No pin holes are illustrated in FIG. 4B and FIG. 4C. However, pin holes may optionally be included in embodiments described by FIG. 4B, FIG. 4C and the accompanying descriptions as well. Described further, each pressure cap 500 may comprise two pin holes 516 disposed on either side of pressure cap 500. Two pin holes 516 may then align with two pin holes 316, 416 on either side of seated pressure cap 300, 400. The alignment of pin holes of pressure cap 500 and body 300, 400 may allow pin 900 to be received therein. Pin 900 may allow spinal fixation system 100 to have a more secured and stable assembly. The use of pin 900 may or may not be necessary or advantageous depending on the particular requirements of specific embodiments of spinal fixation system 100. For example, the inclusion of pin 900 may allow for added security. However, the inclusion of pin 900 may also result in an increase in the number of independent components in system 100. Embodiments of the present disclosure may or may not include pin 900. Such variations may be made without departing from the description herein.

In some embodiments, proximal ends 502, 602 of pressure cap 500, 600 may comprise at least two side walls 506, 606 disposed apart from one another. Sidewalls may be disposed at the top ends of curved surface 510, 610 of pressure cap 500, 600. Sidewalls 506, 606 may be specifically shaped or designed to fit with particular corresponding shapes or designs in selected bodies 300, 400.

In some embodiments, at least one biasing member 508, 608 may be disposed on proximal ends of the side walls 506, 606. Biasing member 508, 608 may be any element or feature operable to create pressure, suspension, or a spring-like effect. In some embodiments, biasing member 508, 608 may be a mechanical design or structure. Various biasing members may be used without departing from the description herein. For example, in some embodiments, the biasing member may be a leaf spring. A leaf spring may comprise a narrow arm of material with a rectangular cross-section. One end of the material 520, 620 may be attached to or may extend from corresponding side wall 506, 606 on which a leaf spring may be disposed. Another end 522, 622 of the leaf spring may be suspended freely above corresponding side wall 506, 606 on which a leaf spring is disposed. The suspension of one end 522, 622 of a leaf spring and fixation of another end of a leaf spring may create a biasing effect or spring-like effect. The elasticity or spring coefficient inherent to the material of a leaf spring may promote a biasing effect or spring-like effect. Accordingly, when another article is disposed on biasing member 508, 608, a spring-like pressure may be effected on the article. In some embodiments, pressure cap 500, 600 may be fitted and secured such that biasing members 508, 608 may be disposed beneath a portion of body 300, 400. Accordingly, biased members 508, 608 may exert a spring-like pressure on a portion of body 300, 400 above it. The resulting effect of a spring-like pressure may be to exert a downward force on head 206 of bone screw 200. As a result, a more secure and stable spinal fixation system 100 may be provided.

In some embodiments, the leaf springs that comprise biasing members 508, 608 may be substantially monolithic with proximal portion 502, 602 of pressure cap 500, 600. Explained further, biasing members 508, 608 may not need to be a separate component that is attached to side walls 506, 606 post-manufacturing. Instead, biasing members 508, 608 may be features that are machined out from a uniform piece of material, such as an implantable metallic material. For example, pressure cap 500, 600 may be machined to have side walls 506, 606. To achieve the design or functionality of biasing members 508, 608, it may be desirable to form a small gap such that a thin, narrow arm of material remains at the top of side walls 506, 606. The feature of the leaf spring may comprise a small gap between the narrow arm of material and side wall 506, 606 on which it is disposed. Accordingly, the small gap may be formed by sawing, drilling, chiseling, or otherwise mechanically removing the material in the space between the desired leaf spring and side walls 506, 606. The resulting article may be pressure cap 500, 600 wherein biasing members 508, 608 may be substantially monolithic with proximal portion 502, 602 of pressure cap 500, 600.

Embodiments of the present disclosure related to monolithic pressure cap 500, 600 may provide for many advantages. For example, pressure cap 500, 600 having a monolithic construction may prevent the need for smaller pieces or articles to be attached to pressure cap 500, 600. For example, an embodiment where bias members 508, 608 are features machined out of a monolithic material may have advantages over an embodiment where biasing members 508, 608 are separate articles that are then adhered to or disposed on pressure cap 500, 600. Examples of said advantages may include increased structural integrity and the possibility of creating smaller articles such as smaller pressure caps with the necessary or desired features.

As seen in FIG. 4A, according to some embodiments of the present disclosure, pressure cap 500 may comprise sidewalls 506 that may have radial protrusions 518. As seen in FIG. 4A, sidewalls 506 may expand radially outward from the core cylinder-like geometry of the pressure cap 500. Radial protrusions 518 may have a curved or annular outer surface. Biasing member 506 or leaf spring that may be disposed on sidewalls 506 may also have a corresponding curved or annular outer surface. In some embodiments, radial protrusion 518 may be operable to be received into undercut 312 of body 300. Further description of how radial protrusions 518 and sidewalls 506 may be received into undercut 312 may be seen in FIG. 5A, FIG. 5B, and the accompanying descriptions.

As seen in FIG. 4B and FIG. 4C, according to some embodiments of the present disclosure, pressure cap 600 may comprise sidewalls 606 that are disposed adjacent to chordal recesses 612 on proximal end 602 of pressure cap 600. As seen in FIG. 4B and FIG. 4C, chordal recess 612 may be an indentation along the cylindrical outer contour of pressure cap 600. Sidewall 606 disposed against chordal recess 612 may have a flat, vertically upward surface. Having a plurality of chordal recesses 612 with sidewalls 606 disposed adjacent to them, wherein sidewalls 606 have a corresponding flat vertical surface, may create a substantially polygonal structure or geometry at proximal end 602 of pressure cap 600. For example, in FIG. 4B and FIG. 4C, the illustrated embodiment may have two sidewalls 606 disposed adjacent to two chordal recesses 612. Two sidewalls 606 may be disposed apart from one another, and the flat vertical surfaces may be parallel to one another. Viewed from above, pressure cap 600 may have a substantially rectangular geometry at proximal end 602, wherein two sides of the rectangular geometry may be comprised of the vertical surfaces of two sidewalls 606. In some embodiments, the polygonal structure or geometry formed by the vertical surfaces along chordal recesses 612 may be operable to be received into corresponding undercut 412 of body 400. In some embodiments, body 400 may have polygonal undercut 412, such as a square-pocket like feature, that may receive the geometry of chordal recess 612 and sidewalls 606 of pressure cap 600. Explained further, proximal end 602 of pressure cap 600 may be operable to fit within undercut 412 when pressure cap 600 is disposed within body 400. The resulting alignment of pressure cap 600 in body 400 may be more secure and may provide for a better fit of the components of spinal fixation system 100.

In some embodiments, distal end 504, 604 of pressure cap 500, 600 may further comprise a surface 614 operable to contact at least a portion of head 206 of bone screw 200. As seen in FIG. 4C, distal end 604 may have surface 614 positioned to contour or mate with head 206 of bone screw 200. In some embodiments, head 206 of bone screw 200 may have a particular shape or geometry, such as being spherically shaped. Accordingly, surface 614 at distal end 604 of pressure cap 600 may have a corresponding shape to contour against head 206. As seen in FIG. 4C, surface 614 may be curved inward to receive head 206 that may have a corresponding curvature. As seen in FIG. 4C, distal end 604 may also comprise distal recess 618 which may be in the center of surface 614. Distal recess 618 may be operable to receive a curved or protruding portion of head 206. Described further, head 206 of bone screw 200 may have a substantially spherical or curved geometry. Accordingly, a portion of head 206 may be contoured against surface 614, and a center portion of the head 206 that may protrude more prominently as a result of its curvature may be disposed within distal recess 618. The size, shape, curvature, or design of surface 614 may be varied for various functional and design reasons. For example, the curvature of surface 614 may be varied to correspond with the curvature of head 206 of bone screw 200.

The surface 614 at distal end 604 of pressure cap 600 may be operable to secure the position of bone screw 200. In some embodiments, surface 614 may be operable to provide a degree of friction or frictional adherence to head 206. Accordingly, surface 614 may "grip" head 206 and allow for added security or stability of spinal fixation system 100. Accordingly, in some embodiments, it may be advantageous to increase the size or surface area of surface 614 so as to allow for maximum contact between surface 614 and head 206. One of ordinary skill in the art would appreciate that the aforementioned "gripping" quality of surface 614 may allow for fewer components in spinal fixation system 100, as separate components to provide for a secure mating of pressure cap 600 and bone screw 200 may no longer be necessary. Such example embodiments may be particular advantageous for use in pediatric settings or as spinal fixation system 100 in a pediatric patient. In the pediatric setting, it may not be advantageous to provide too many components as each individual component may be small, and may be difficult to handle or maneuver. Furthermore, a high number of components may lead to an increase in the likelihood that small fragments may break off from spinal fixation system 100.

The size and dimensions of pressure cap 500, 600 may be varied for various functional and design reasons. In some embodiments, pressure cap may have a height of about 0.15 inches to about 0.35 inches. In some embodiments, where body 300 may be easily disengaged from bone screw 200 secured in a bone, pressure cap 500 may have a height of about 0.2 inches. In some embodiments, where spinal fixation system 100 may be used in a pediatric setting, the pressure cap 600 may have a height of about 0.25 inches.

Figure 5A:
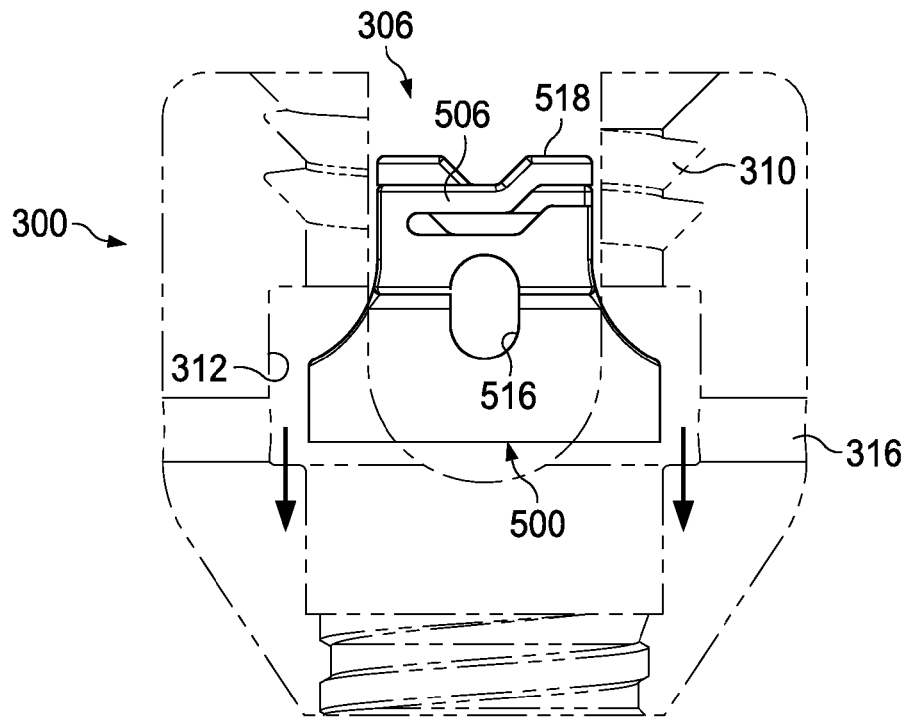
FIG. 5A illustrates a profile view of a pressure cap during assembly with a body according to a specific example embodiment of the disclosure.
Figure 5B:
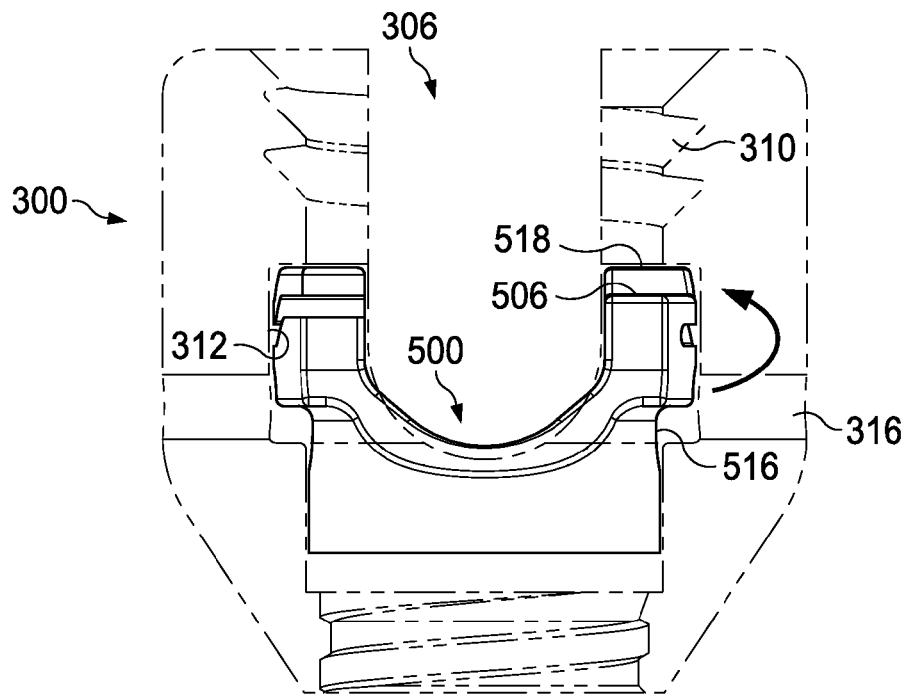
FIG. 5B illustrates a profile view of a pressure cap fitted in the body after assembly according to a specific example embodiment of the disclosure.

Referring now to FIG. 5A and FIG. 5B, profile views of pressure cap 500 during and after assembly with body 300 according a specific example embodiment of the disclosure are illustrated. More specifically, FIG. 5A and FIG. 5B illustrate how pressure cap 500 may be received into body 300 and rotated into a secured position. In FIG. 5A and FIG. 5B, dotted lines are used to depict body 300 so as to provide a see-through view of the body 300 and allow for an illustration of the movement of pressure cap 500 as it is being secured. In FIG. 5A, pressure cap 500 may be lowered into body 300. Arrows shown in FIG. 5A and FIG. 5B are illustrative of how pressure cap 500 may be lowered into body 300. Pressure cap 500 may be positioned such that radial protrusions 518 of sidewalls 506 may align with mounting rod receiving channel 306.

Mounting rod receiving channel 306 may form openings along the outer walls of body 300. Openings of mounting rod receiving channel 306 may extend down along a portion of the length of body 300. Radial protrusions 518 of sidewalls 506 may be enlarged portions such that radial protrusions may not fit or be operable to slide into body 300 unless radial protrusions 518 are aligned with openings of mounting rod receiving channel 306. An opening formed by mounting rod receiving channel 306 may be operable to receive pressure cap 500, and more specifically, radial protrusions 518 of pressure cap 500. Once received, pressure cap 500 may be lowered or slid down a longitudinal axis of body 300. Pressure cap 500 may be lowered until radial protrusions sit or rest at a distal end of mounting rod receiving channel 306.

Once pressure cap 500 is completely lowered, pressure cap 500 may be seated such that proximal end 502 of pressure cap 500 is within the distal end of mounting rod receiving channel 306. Described further, proximal end 502 of pressure cap 500 may be distal to internal thread 310 at proximal end of mounting rod receiving channel 306. In this position, pin hole 516 of pressure cap 500 may be aligned orthogonally to pin hole 316 of body 300.

To be positioned into a secure or locked position, pressure cap 500 may be rotated by a ¼ turn (e.g. 90°) such that radial protrusions 518 of pressure cap 500 are received into undercut 312 of body 300. As previously described, undercut 312 of body 300 may be a recess disposed in body 300 that may be enlarged from the spacing used to house the rest of pressure cap 500. Accordingly, radial protrusions 518, which may be enlargements extending from sidewalls 506 may be received into undercut 312. In some embodiments, radial protrusions 518 and corresponding undercut 312 may have corresponding curvature or annular geometry such that radial protrusions 518 may be received into undercut 312 by turning pressure cap 500. As seen in FIG. 5B, a profile view of pressure cap 500 wherein radial protrusions 518 have been received into the undercut 312 is illustrated. As seen in FIG. 5B, when pressure cap 500 has been secured, pin hole 516 of pressure cap 500 may be fully aligned with the pin hole 316 of the body 300. Accordingly, aligned pin holes 516, 316 may be operable to receive pin 900 therein.

Furthermore, the secured pressure cap may allow mounting rod 700 to be securely received into the length of mounting rod receiving channel 306.

Figure 6A:
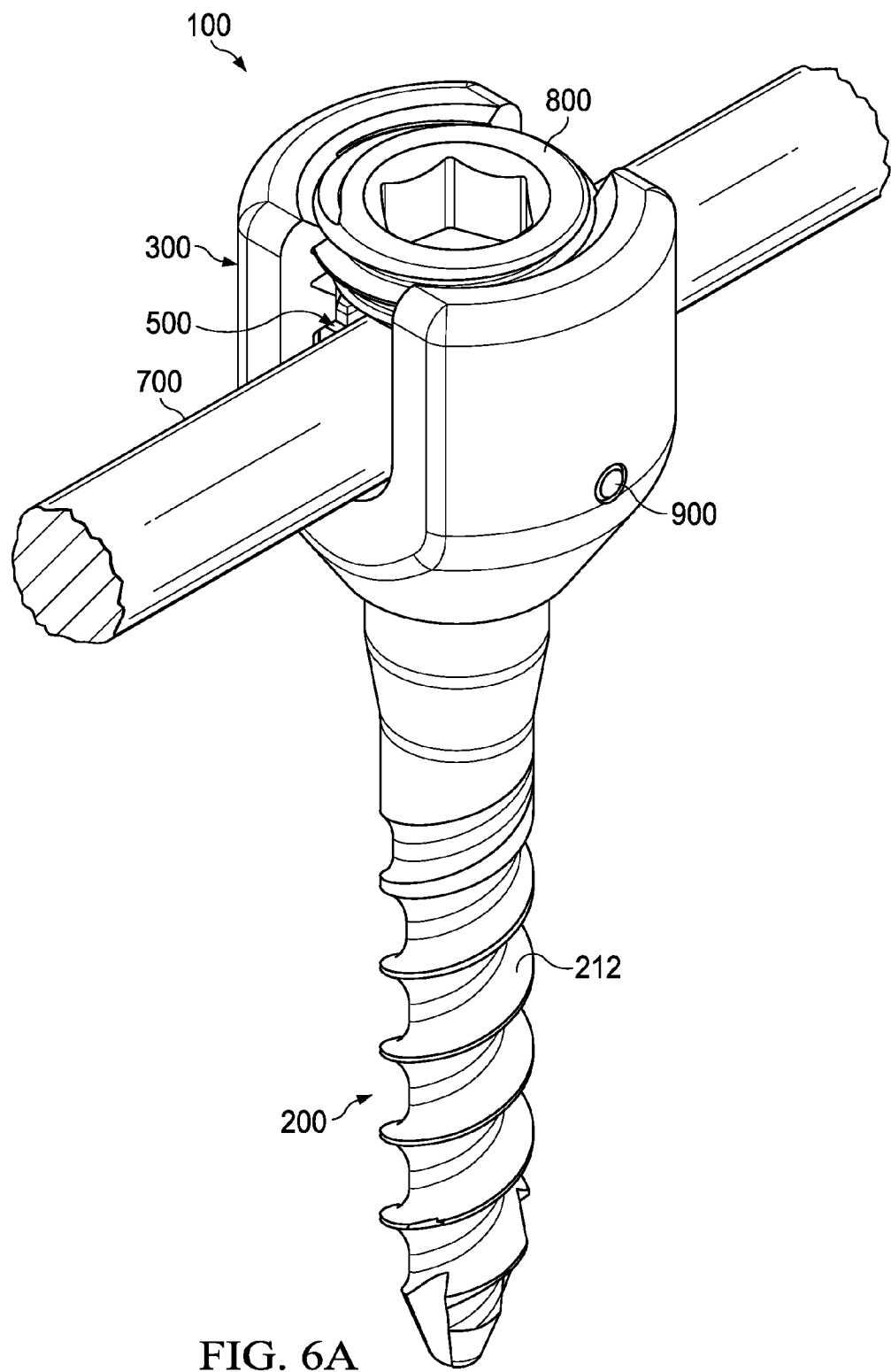
FIG. 6A illustrates a perspective view of a pedicle screw system according to a specific example embodiment of the disclosure.
Figure 6B:
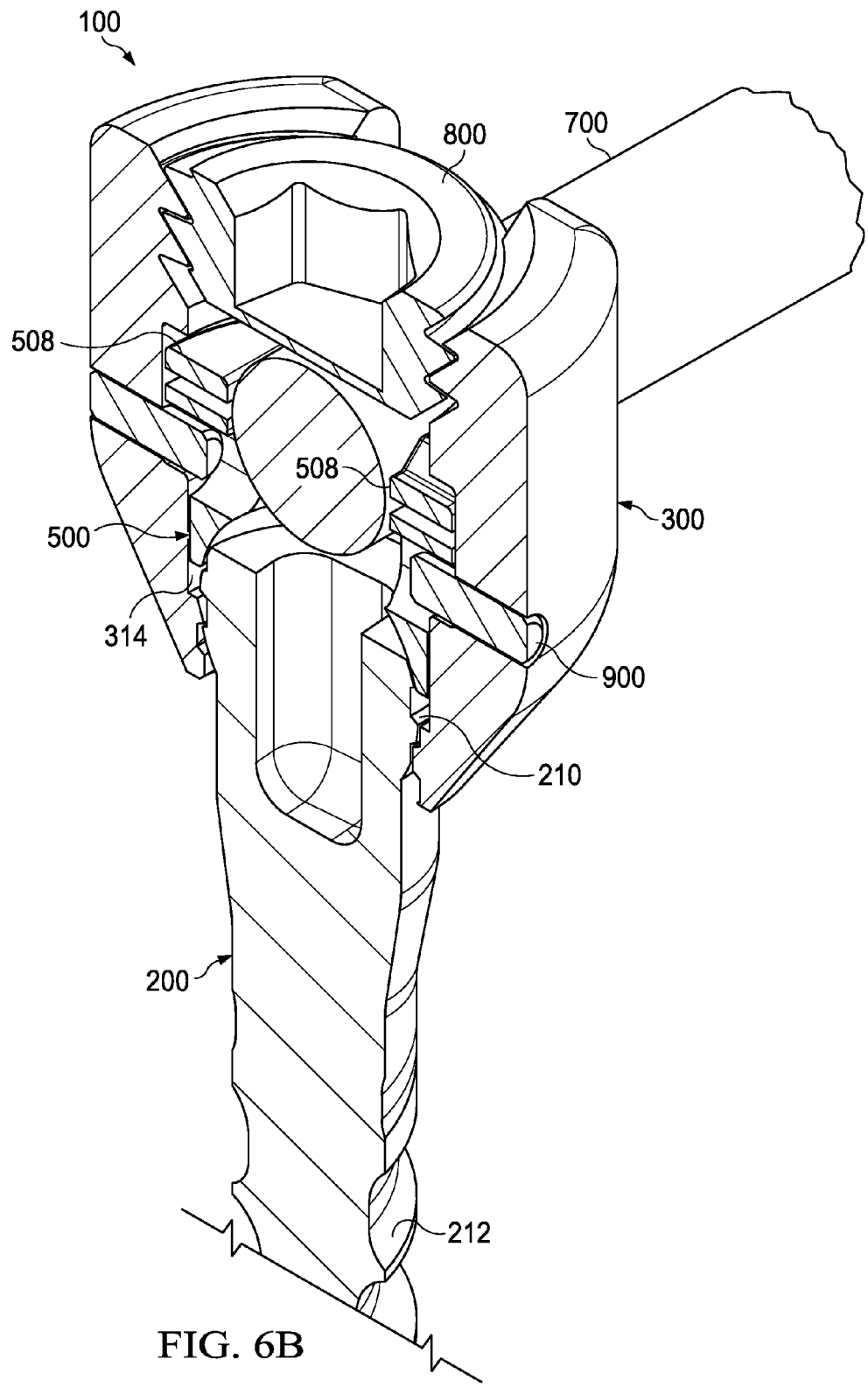
FIG. 6B illustrates a perspective cross-sectional view of a pedicle screw system according to a specific example embodiment of the disclosure.

Referring now to FIG. 6A and FIG. 6B, a perspective view and a perspective cross-sectional view of pedicle screw system 100 assembled according to the present disclosure is illustrated. More specifically, FIG. 6A and FIG. 6B illustrate an exemplary embodiment of the present disclosure wherein body 300 may be easily disengaged from bone screw 200, even after bone screw 200 has been affixed or secured in a bone. As seen in FIG. 6A and FIG. 6B, spinal fixation system 100 may comprise bone screw 200, body 300, pressure cap 500, mounting rod 700, compression element 800, and pin 900.

In some embodiments, as seen in the cross-sectional view provided by FIG. 6B, spinal fixation system 100 may comprise threaded recess 314 disposed at the distal end of body 300. Threaded recess 314 may be engaged with threaded region 210 of head 206 of bone screw 200. Threaded recess 314 and threaded region 210 may be easily engaged or disengaged. In some embodiments, threaded recess 314 and threaded region 210 may be operable to engage or disengage by means of a full turn (e.g. 360°). As seen in FIG. 6A and FIG. 6B, threaded region 210 of bone screw 200 comprises a separate threading than external threading 212. Accordingly, the engaging or disengaging against threaded region 210 may not disturb the engagement of external thread 212 in, for example, a pedicle portion of the spine.

As seen in FIG. 6B, in some embodiments, biasing members 508 of pressure cap 500 may exert an upward, spring-like pressure. Said pressure may be exerted upward against a portion of body 300. The resulting pressure may also create a downward force of pressure cap 500 against bone screw 200. Accordingly, a more secure and stable system in body 300 of spinal fixation system 100 may be provided. Also depicted in FIG. 6A and FIG. 6B is pin 900, which may be inserted in the alignment of pin hole 516 of pressure cap 500 with pin hole 316 of body 300. An insertion of pin 900 may secure the pressure cap 500 into alignment with body 300.

Figure 7B:
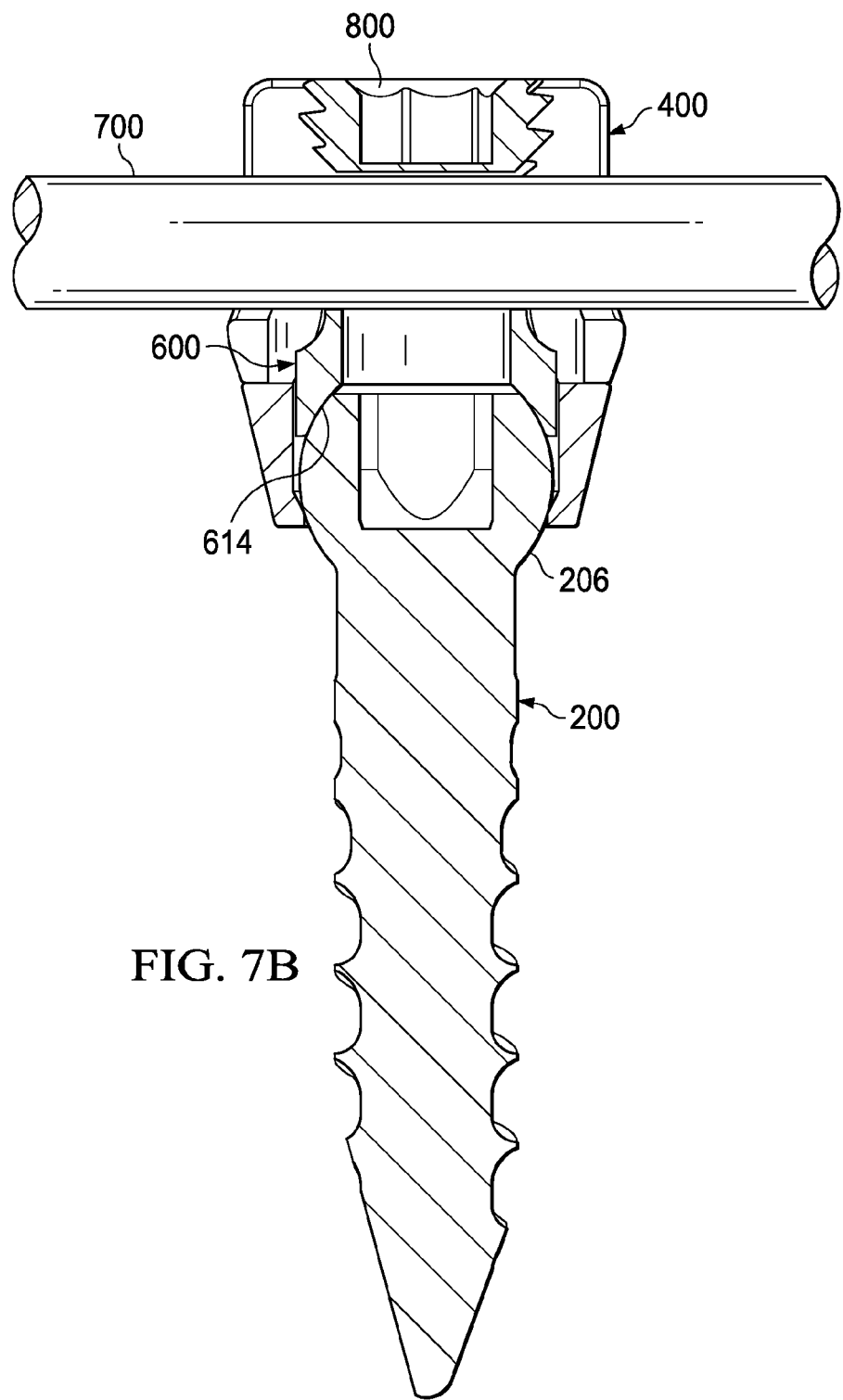
FIG. 7B illustrates another profile cross-sectional view of a pedicle screw system according to a specific example embodiment of the disclosure.
Figure 8:
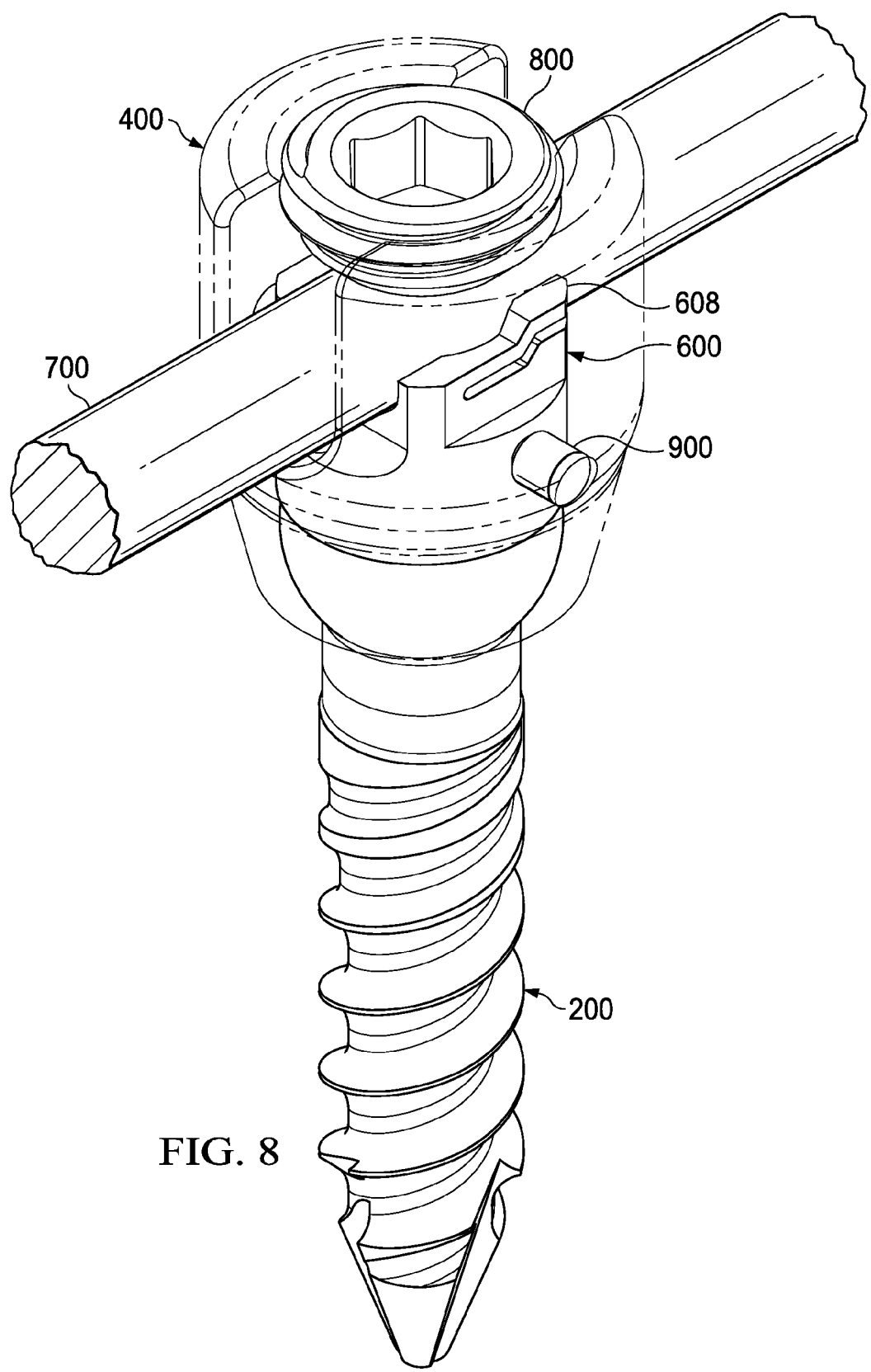
FIG. 8 illustrates a see-through perspective view of a pedicle screw system according to a specific example embodiment of the disclosure.

Referring now to FIG. 7A, FIG. 7B, and FIG. 8, a profile cross-sectional view, another profile cross-sectional view, and a see-through perspective view, respectively, of pedicle screw system 100 according a specific example embodiment of the present disclosure are illustrated. More specifically, FIG. 7A, FIG. 7B, and FIG. 8 illustrate an exemplary embodiment of the present disclosure operable for use in a pediatric setting. As seen in FIG. 6A and FIG. 6B, the spinal fixation system may comprise bone screw 200, body 400, pressure cap 600, mounting rod 700, compression element 800, and pin 900.

As seen in FIG. 7A and FIG. 8, in some embodiments, biasing members 608 of pressure cap 600 may exert an upward, spring-like pressure. Said pressure may be exerted upward against a portion of pressure cap 400. The resulting pressure may also create a downward force of pressure cap 600 on bone screw 200. Accordingly, a more secure and stable system in body 400 of spinal fixation system 100 may be provided.

As seen in FIG. 7A and FIG. 7B, in some embodiments, spinal fixation system 100 may comprise surface 614 on distal end 604 of pressure cap 600. Surface 614 may be operable to contact at least a portion of head 206 of bone screw 200. Surface 614 at distal end 604 of pressure cap 600 may have a shape that may correspond to or contour against head 206. Accordingly, a portion of head 206 may be contoured against surface 614.

As seen in FIG. 7A and FIG. 7B, in some embodiments, spinal fixation system 100 may comprise body 400 that comprises a two-piece construction. More specifically, body 400 may be comprise an upper portion and a lower portion. Explained further, body 400 may comprise two separately machined or manufactured components that may then be interlocked or otherwise disposed together to form the entirety of body 400 described herein. Such variations may be made to body 400 without departing from the description herein.

In some embodiments, a pedicle screw system 100 depicted in FIG. 7A and FIG. 7B may be advantageous for use in pediatric settings. For pediatric use, it may be desirable to have smaller pedicle screw systems 100 and/or small components therein. In some embodiments, body 400 may comprise a height of about 0.36 inches. In some embodiments, pressure cap 600 may comprise a height of about 0.25 inches. As seen in FIG. 7A and FIG. 7B, pressure cap 600 may have surface 614 (see FIG. 4C) which may contour against at least a portion of head 206 of bone screw 200. Surface 614 may have sufficient surface area to effectively "grip" or exert substantial friction upon or a portion of head 206 of bone screw 200. The "gripping" effect or friction between head 206 and surface 614 may be sufficient to form a secure connection for a stable pedicle screw system 100. As in FIG. 7A and FIG. 7B, embodiments of the present disclosure may advantageously remove the need for a separate spring component or biasing component. Accordingly, embodiments of the present disclosure may advantageously reduce the number of separate components or moving components in need of assembly in pedicle screw system 100.

The present disclosure relates, in some embodiments, to methods of affixing bone screw system 100 to a bone, such as a pedicle portion of a spine. A method may comprise providing bone screw 200, wherein bone screw 200 may comprise head 206 at proximal end 202, bone connection element 208 at distal end 204, and threaded region 210 at head 206. The method may further comprise providing body 300 wherein body 300 may comprise proximal end 302, distal end 304, mounting rod receiving channel 312 disposed at proximal end 302 of the body; bone screw head receiving channel 308 disposed at distal end 304 of body 300, undercut 312, and threaded recess 314 on distal end 304 of body 300. Proximal end 302 and distal end 304 may be disposed along a longitudinal axis.

A method may further comprise securing bone screw 200 to body 300 by engaging threaded region 210 with threaded recess 314 of body 300 by means of a full turn (e.g. 360°). A method may further comprise securing bone connection element 208 of bone screw 200 to a bone.

A method may further comprise providing pressure cap 500. Pressure cap 500 may comprise proximal end 502 and distal end 504. Proximal end 502 may comprise at least two radial protrusions 518 disposed apart from each other, and at least one biasing member 508 disposed on each radial protrusion 518.

A method may further comprise disposing pressure cap 500 in body 300 through mounting rod receiving channel 312. A method may further comprise securing pressure cap 500 into body 300 by means of a ¼ turn (e.g. 90°) such that radial protrusions 518 are received into undercut 312 of body 300.

In some embodiments, threaded recess 314 may be operable to engage or disengage with threaded region 210 of head 206 of bone screw 200 by means of a full turn. As previously described, such features may advantageously allow for body 300 to be disengaged from bone screw 200 after bone screw 200 has already been secured into a bone. For example, during a surgical procedure a surgeon may fit bone screw 200 with a selected body. Then, the surgeon may secure this combination of bone screw 200 and the selected body into a bone region by, for example, screwing bone connection element 208 into the bone. However, after securing bone connection element 208 into the bone, it may become apparent that the body selected was not ideal or that a differently designed or differently sized body may be more appropriate. A different body may be more appropriate as it may promote a more secure fit of spinal fixation system 100 with the bone, or it may promote a better alignment of mounting rod 700 through a plurality of bodies 300.

According, the method may further comprise disengaging threaded region 210 from threaded recess 314. The disengagement may be accomplished by means of a full turn of body 300. The method may then further comprise selecting a different body which may then be engaged with threaded region 210 through a corresponding threaded recess in the selected body.

One of ordinary skill in the art would appreciate that any of the features, variations, and other embodiments described above for the articles and systems of the present disclosure may apply to the presently disclosed method without departing from there description herein.

One of ordinary skill in the art would having the benefit of the present disclosure would appreciate that any of the embodiments of the present disclosure, the materials may be chosen and may be varied to fit a number of functional and design considerations. In some embodiments, the bone screw 200, body, 300, 400, pressure cap 500, 600, mounting rod 700, compression element 800, and pin 900 may be made of materials such as Titanium, Ti-6Al-4V, stainless steel or CoCr. However, one of ordinary skill in the art would appreciate that any implantable metallic material may be used without departing from the description herein. Furthermore, the material of each component may be independently selected and the material of component may vary from one another without departing from the description herein.

As will be understood by those skilled in the art who have the benefit of the instant disclosure, other equivalent or alternative compositions, devices, methods, and systems for a modular pedicle screw can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value+/−about 10%, depicted value+/−about 50%, depicted value+/−about 100%) and/or a range endpoint. With respect to the former, a value of 50 depicted in an example, table, and/or drawing may form the basis of a range of, for example, about 45 to about 55, about 25 to about 100, and/or about 0 to about 100.

All or a portion of a device and/or system for a modular pedicle screw may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

What is claimed is:

1. A spinal fixation system, comprising:
   at least one bone screw comprising:
      a head at a proximal end; and
      a bone connection element at a distal end;
   at least one body comprising:
      a proximal end;
      a distal end;
      a mounting rod receiving channel disposed at the proximal end of the body; and
      a bone screw head receiving channel disposed at the distal end of the body;
      wherein the proximal end and distal end are disposed along a longitudinal axis; and
      wherein a proximal portion of the mounting rod receiving channel comprises an internal thread for receiving a compression element; and
   at least one pressure cap comprising:
      a proximal end comprising:
         at least two side walls disposed apart from each other, wherein the at least two side walls define a groove therebetween, a distal end of the groove comprising a curved surface operable to mate with a mounting rod received within the groove, wherein an inner surface of each of the at least two side walls comprises a vertical surface extending proximally from the curved surface; and
         at least one biasing member disposed on a proximal end of each side wall, such that a portion of the biasing member is suspended freely above a majority of a corresponding side wall to allow the pressure cap to contact the body via the biasing member; and
      a distal end comprising;
         a surface operable to contact at least a portion of the head of the bone screw;
      wherein the pressure cap is configured to be disposed within the body and between the mounting rod and the bone screw; and wherein when the mounting rod is biased against the proximal end of the pressure cap, the distal end of the pressure cap is operable to exert pressure on the bone screw.

2. The spinal fixation system according to claim 1, wherein the head of the bone screw has a substantially spherical surface.

3. The spinal fixation system according to claim 1, wherein the bone connection element comprises an external thread operable to be secured into a pedicle portion of a spine.

4. The spinal fixation system according to claim 1, wherein the mounting rod receiving channel is operable to receive a mounting rod at an angle substantially orthogonal to the longitudinal axis of the body.

5. The spinal fixation system according to claim 1, wherein the bone screw head receiving channel is sized to securely receive the bone screw head.

6. The spinal fixation system according to claim 1, wherein the curved surface is operable to align with a portion of the mounting rod.

7. The spinal fixation system according to claim 1, wherein the bone screw, the body, the mounting rod, the compression element, and the pressure cap each comprises material independently selected from the group consisting titanium, titanium alloy, stainless steel, cobalt chrome, or any combination thereof.

8. The spinal fixation system according to claim 1,
wherein the body further comprises a pin hole disposed orthogonal to the longitudinal axis of the body;
wherein the pressure cap further comprises a pin hole disposed orthogonal to the longitudinal axis of the body; and
wherein the pin hole of the body and the pin hole of the pressure cap align and are operable to receive a pin.

9. The spinal fixation system according to claim 8, wherein the pin comprises material selected from the group consisting titanium, titanium alloy, stainless steel, cobalt chrome, and any combination thereof.

10. The spinal fixation system according to claim 1,
wherein the body further comprises an undercut adjacent to the mounting rod receiving channel and distal to the internal thread;
wherein each of the side walls comprises a radial protrusion operable to fit within the undercut when the pressure cap is disposed within the body.

11. The spinal fixation system according to claim 1, wherein an inner diameter of the portion of the biasing member is operable to bias the pressure cap against the head of the bone screw.

12. The spinal fixation system according to claim 11, wherein the biasing member is a leaf spring.

13. The spinal fixation system according to claim 12, wherein the leaf spring is monolithic with a proximal portion of the pressure cap.

14. The spinal fixation system according to claim 1,
wherein the head of the bone screw further comprises a threaded region; wherein the distal end of the body further comprises a threaded recess; and
wherein the threaded region is operable to engage or disengage with the threaded recess.

15. The spinal fixation system according to claim 14, wherein the threaded region is operable to engage or disengage with the threaded recess by means of a full turn.

16. The spinal fixation system according to claim 15, wherein the body has a monolithic construction.

17. The spinal fixation system according to claim 1, wherein the body is about 0.45 inches high.

18. The spinal fixation system according to claim 1, wherein the pressure cap is about 0.2 inches high.

19. The spinal fixation system according to claim 1, wherein the body is a two-piece construction.

20. The spinal fixation system according to claim 19, wherein the body is about 0.36 inches high.

21. The spinal fixation system according to claim 19, wherein the pressure cap is about 0.25 inches high.

22. The spinal fixation system according to claim 19,
wherein the body further comprises an undercut adjacent to the mounting rod receiving channel and distal to the internal thread;
wherein each of the side walls is disposed adjacent to a chordal recess on the proximal end of the pressure cap;
wherein the proximal end of the pressure cap is operable to fit within the undercut when the pressure cap is disposed within the body.

23. A method of affixing a bone screw system, the method comprising:
providing a bone screw, wherein the bone screw comprises
a head at a proximal end;
a bone connection element at a distal end; and
a threaded region on the head;
providing a body, wherein the body comprises
a proximal end;
a distal end;
a mounting rod receiving channel disposed at the proximal end of the body;
a bone screw head receiving channel disposed at the distal end of the body; and
a threaded recess on the distal end of the body;
wherein the proximal end and distal end are disposed along a longitudinal axis;
securing the bone screw to the body by fully engaging the threaded region of the head of the bone screw with the threaded recess of the body by means of a partial turn;
securing the bone connection element in a bone;
providing a pressure cap; and
disposing the pressure cap in the body through the mounting rod receiving channel.

24. The method of claim 23, the method further comprising:
fully disengaging the threaded region of the head of the bone screw with the threaded recess of the body by means of a partial turn.

* * * * *